(12) United States Patent
Carroll et al.

(10) Patent No.: US 7,399,762 B2
(45) Date of Patent: Jul. 15, 2008

(54) OPIOID RECEPTOR AGONIST COMPOUNDS AND THEIR USE IN TREATMENT OF PAIN

(75) Inventors: Frank Ivy Carroll, Research Triangle Park, NC (US); Hernan A. Navarro, Chapel Hill, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 233 days.

(21) Appl. No.: 11/113,158

(22) Filed: Apr. 25, 2005

(65) Prior Publication Data

US 2006/0241135 A1 Oct. 26, 2006

(51) Int. Cl.
*A61K 31/53* (2006.01)
*A61K 31/497* (2006.01)
*A61K 31/44* (2006.01)

(52) U.S. Cl. .................. 514/241; 514/247; 514/253; 514/339

(58) Field of Classification Search .................. 514/241, 514/247, 253, 339
See application file for complete search history.

(56) References Cited

U.S. PATENT DOCUMENTS

| | | | |
|---|---|---|---|
| 4,529,736 A | 7/1985 | McKenzie et al. | |
| 5,128,118 A | 7/1992 | Carroll et al. | |
| 5,141,959 A | 8/1992 | Carroll et al. | |
| 5,298,499 A | 3/1994 | Carroll et al. | |
| 5,380,848 A | 1/1995 | Kuhar et al. | |
| 5,413,779 A | 5/1995 | Kuhar et al. | |
| 5,496,953 A | 3/1996 | Kuhar et al. | |
| 5,736,123 A | 4/1998 | Carroll | |
| 5,831,095 A | 11/1998 | Gonzalez et al. | |
| 5,935,953 A | 8/1999 | Kuhar et al. | |
| 6,123,917 A | 9/2000 | Carroll | |
| 6,329,520 B1 | 12/2001 | Carroll et al. | |
| 6,358,492 B1 | 3/2002 | Kuhar et al. | |
| 6,416,735 B1 | 7/2002 | Carroll et al. | |
| 6,479,509 B1 | 11/2002 | Carroll | |
| 6,531,481 B2 | 3/2003 | Carroll et al. | |
| 6,531,483 B1 | 3/2003 | Kuhar et al. | |
| 6,538,010 B1 * | 3/2003 | Carroll | 514/339 |
| 6,552,032 B2 | 4/2003 | Carroll et al. | |
| 6,559,159 B2 * | 5/2003 | Carroll et al. | 514/282 |
| 6,593,348 B2 | 7/2003 | Carroll et al. | |
| 6,706,880 B2 | 3/2004 | Carroll et al. | |
| 6,900,228 B1 | 5/2005 | Carroll et al. | |
| 2002/0132828 A1 | 9/2002 | Carroll et al. | |
| 2002/0188003 A1 | 12/2002 | Kuhar et al. | |
| 2003/0158415 A1 | 8/2003 | Carroll et al. | |
| 2003/0176434 A1 | 9/2003 | Carroll | |
| 2003/0203934 A1 | 10/2003 | Kuhar et al. | |
| 2004/0146518 A1 | 7/2004 | Carroll et al. | |

OTHER PUBLICATIONS

Peng et al, Journal of Medicinal Chemistry (2005), 48(5), 1620-1629.*

(Continued)

*Primary Examiner*—Janet L. Andres
*Assistant Examiner*—Raymond Covington
(74) *Attorney, Agent, or Firm*—Oblon, Spivak, McClelland, Maier & Neustadt, P.C.

(57) ABSTRACT

Structurally novel opioid receptor agonists are provided, and the use of these agonists in treatment of chronic and/or acute pain.

18 Claims, 3 Drawing Sheets

OTHER PUBLICATIONS

Carroll et al, Journal of Medicinal Chemistry (2004), 47(2), 281-284.*

Bertha et al, Journal of Medicinal Chemistry (1995), 38(9), 1523-37.*

A.F. Abdel-Magid, et al., "Reductive Amination of Aldehydes and Ketones with Sodium Triacetoxyborohydride. Studies on Direct and Indirect Reductive Amination Procedures", J. Org. Chem., 61, 1996, pp. 3849-3862.

J.V. Aldrich, et al., "Narcotic Analgesics", Burger's Medicinal Chemistry and Drug Discover, vol. 6, Chapter 7, 2003, pp. 329-481.

D.S. Bruce, et al., "Circannual Variations in Bear Plasma Albumin and its Opioid-Like Effects on Guinea Pig Ileum", Pharmacology Biochemistry and Behavior, vol. 53, No. 4, 1996, pp. 885-889.

Y. Chen, et al., "Molecular Cloning and Functional Expression of a μ-Opioid Receptor From Rat Brain", Molecular Pharmacology, vol. 44, 1993, pp. 8-12.

A.D. Corbett, et al., "Dynorphin 1-8 and Dynorphin 1-9 are Ligands for the κ-Subtype of Opiate Receptor", Nature, vol. 299, Sep. 2, 1982, pp. 79-81.

C.M. Bertha, et al., "Probes for Narcotic Receptor-Mediated Phenomena. 21. Novel Derivatives of 3-(1,2,3,4,5,11-Hexahydro-3-Methyl-2,6-Methano-6H-Azocino [4,5-b] indol-6-yl)-Phenols With Improved δ Opioid Receptor Selectivity", J. Med. Chem., 39, 1996, pp. 2081-2086.

C.J. Evans, et al., "Cloning of a Delta Opioid Receptor by Functional Expression", Science, vol. 258, Dec. 18, 1992, pp. 1952-1955.

X.-P. Gu, et al., "2-Chloro-1-(Chloromethyl)Ethyl Methoxymethyl Ether as a Reagent for Acetonylation of Alcohols and Phenol", J. Org. Chem., 51, 1986, pp. 5425-5427.

X.-P. Gu, et al., "2-(Chloromethyl)-3,5-Dioxahex-1-Ene. An Effective Acetonylating Reagent", J. Org. Chem., 52, 1987, pp. 3192-3196.

X.-P. Gu, et al, "Catalytic Acetonylation of Cyclic 1,3-Dicarbonyl-Systems by 2-(Chloromethyl)-3,5-Dioxa-1-Hexene", Synthesis, 1988, pp. 535-537.

R.M. Jones, et al., "Mutational Evidence for a Common κ Antagonist Binding Pocket in the Wild-Type κ and Mutant μ [K303E] Opioid Receptors", Journal of Medicinal Chemistry, vol. 41, No. 25, Dec. 3, 1998, pp. 4911-4914.

B.L. Kieffer, et al., "The δ-Opioid Receptor: Isolation of a CDNA by Expression Cloning and Pharmacological Characterization", Proc. Natl. Acad. Sci, USA, vol. 89, Dec. 1992, pp. 12048-12052.

A. Marki, et al., "μ-Opioid Receptor Specific Antagonist Cyprodime: Characterization by in vitro Radioligand and [35S]GTPγS Binding Assays", European Journal of Pharmacology, 383, 1999, pp. 209-214.

F. Meng, et al., "Cloning and Pharmacological Characterization of a Rat κ Opioid Receptor", Proc. Natl. Acad. Sci. USA, vol. 90, Nov. 1993, pp. 9954-9958.

M. Minami, et al., "Cloning and Expression of a CDNA for the Rat κ-Opioid Receptor", FEBS, vol. 329, No. 3, Aug. 1993, pp. 291-295.

M. Nishi, et al., "CDNA Cloning and Pharmacological Characterization of an Opioid Receptor With High Affinities for κ-Subtype-Selective Ligands", FEBS, vol. 330, No. 1, Sep. 1993, pp. 77-80.

S.L. Olmsted, et al., "A Remarkable Change of Opioid Receptor Selectivity on the Attachment of a Peptidomimetic κ Address Element to the δ Antagonist, Natrindole: 5'-[N2-Alkylamidino)Methyl]Naltrindole Derivatives as a Novel Class of κ Opioid Receptor Antagonists", J. Med. Chem., 36, 1993, pp. 179-180.

C.B. Pert, et al., "Opiate Receptor: Demonstration in Nervous Tissue", Science, vol. 179, Mar. 9, 1973, pp. 1011-1014.

P.S. Portoghese, et al., "Binaltorphimine and Mor-Binaltorphimine, Potent and Selective κ-Opioid Receptor Antagonists", Life Sciences, vol. 40, 1987, pp. 1287-1292.

P.S. Portoghese, "The Design of δ-Selective Opioid Receptor Antagonists", II Farmaco, vol. 48, No. 2, 1993, pp. 243-251.

R. Schwyzer, "ACTH: A Short Introductory Review", Annals New York Acad of Sciences, 1977, pp. 3-26.

P.L. Smiley, et al., "Effects of Cocaine on Extrapyramidal and Limbic Cynorphin Systems", Journal of Pharmacology and Experimental Therapeutics, vol. 253, No. 3, 1990, pp. 938-943.

R. Spanagel, et al., "Modulation of Morphine-Induced Sensitization by Endogenous κ Opioid Systems in the Rat", Neuroscience Letters, 153, 1993, pp. 232-236.

R. Spanagel, et al. "Opposing Tonically Active Endogenous Opioid Systems Modulate the Mesolimbic Dopaminergic Pathway", Proc. Natl. Acad. Sci. USA, vol. 89, Mar. 1992, pp. 2046-2050.

J.B. Thomas, et al., "Investigation of the N-Substituent Conformation Governing Potency and μ Receptor Subtype-Selectivity in (+)-(3R,4R)-Dimethyl-4-_3-Hydroxyphenyl)-Piperidine Opioid Antagonists", J. Med. Chem., 41, 1998, pp. 1980-1990.

J.B. Thomas, et al., "N-Substituted 9β-Methyl -5-(3-Hydroxyphenyl) Morphans are Opioid Receptor Pure Antagonists", J. Med. Chem., 41, 1998, pp. 4143-4149.

J.B. Thomas, et al., "A Stereoselective Synthetic Approach to N-Alkyl-4β-Methyl-5-Phenylmorphans", Tetrahedron Letters, 40, 1999, pp. 403-406.

R. C. Thompson, et al., "Cloning and Pharmacological Characterization of a Rat μ Opioid Receptor", Neuron, vol. 11, Nov. 1993, pp. 903-913.

K.A. Trujillo, et al., "Changes in Prodynorphin Peptide Content Following Treatment With Morphine or Amphetamine: Possible Role in Mechanisms of Action of Drug of Abuse", NIDA Res Mono, 95, 1989, pp. 550-551.

J.R. Volpicelli, et al., "Effect of Anltrexone on Alcohol "High" in Alcoholics", Am. J. Psciatry, 152, Apr. 1995, pp. 613-615.

J.R. Volpicelli, et al., "Naltrexone in the Treatment of Alcohol Dependence", Arch Gen Psychiatry, vol. 49, Nov. 1992, pp. 876-880.

J.-B. Wang, et al., "Human β Opiate Receptor CDNA and Genomic Clones, Pharmacologic Characterization and Chromosomal Assignment", FEBS Letters, 338, 1994, pp. 217-222.

J.A. Werner, et al., "Synthesis of Trans-3,4-Dimethyl -4-(3-Hydroxyphenyl) Piperidine Opioid Antagonists: Application of the CIS-Thermal Elimination of Carbonates to Alkaloid Synthesis", J. Org. Chem., 61, 1996, pp. 587-597.

J.E. Zadina, et al., "A Potent and Selective Endogenous Agonist for the -Opiate Receptor", Nature, vol. 386, Apr. 3, 1997, pp. 499-502.

D.M. Zimmerman, et al., "Synthesis and Analgesic Properties of N-Substituted Trans-4A-Aryldecahydroisoquinolines", J. Med. Chem., 31, 1988, pp. 555-560.

D.M. Zimmerman, et al., "Structure-Activity Relationships of Trans-3,4-Dimethyl-4-(3-Hydroxyphenyl) Piperidine Antagonists for μ- and κ-Opioid Receptors", Journal of Medicinal Chemistry, vol. 36, No. 20, Oct. 1, 1993, pp. 2833-2841.

D.M. Zimmerman, et al., "New Structural Concepts for Narcotic Antagonists Defined in a 4-Phenylpiperidine Series", Nature, vol. 275, Sep. 28, 1978, pp. 332-334.

D.M. Zimmerman, et al., "Structural Requirements for Affinity and Intrinsic Activity at the Opiate Receptor Defined in 4-Phenylpiperidine and Related Series", NIDA Research Monograph, 41, 1982, pp. 112-118.

D.M. Zimmerman, et al., "Opioid Receptor Antagonists: Comparisons of Trans-3,4-Dimethyl-4-Phenylpiperidines and Their Use in the Development of a Model of Opioid Receptors", Pharmacol. Rev. in press, 1992, pp. 2-22.

D.M. Zimmerman, et al., "Further Investigation of Novel 3-Methyl-4-Phenylpiperidine Narcotic Antagonists", Proc. 40 CPPDD, 1978, pp. 237-247.

G. Nunez, et al., "Opioides y Sistema Immune", Rev. Med. Chile, 127, 1999, pp. 341-348.

U.S. Appl. No. 11/272,492, filed Nov. 14, 2005, Carroll.

U.S. Appl. No. 11/113,158, filed Apr. 25, 2005, Carroll et al.

* cited by examiner

FIGURE 1

1, $R_1 = R_2 = H$
2, $R_1 = R_2 = COCH_3$

Figure 2

Reagents: a) n-BuLi then ClCH$_2$C(OCH$_2$OCH$_3$)CH$_2$ then 1N HCl, MeOH: b) HONH$_2$·HCl, EtOH; c) Na, i-PrOH, toluene; d) phthalic anhydride, toluene, heat; e) 1-chloroethylchloroformate, dichloroethane; f)NaBH(OAc)$_3$, RCHO; g) HNNH$_2$, EtOH reflux; h) 48% HBr, glacial HOAc, reflux; i) HCl then H(OCH$_3$)$_3$; j) LiAlH$_4$, THF; k) BBr$_3$, CH$_2$Cl$_2$, -78 °C.

Figure 3. Compound 2.8 Agonist Activity

Figure 4. Compound 2.11 Agonist Activity

OPIOID RECEPTOR AGONIST COMPOUNDS AND THEIR USE IN TREATMENT OF PAIN

BACKGROUND OF THE INVENTION

1. Field of the Invention

The present invention relates to opioid receptor agonist compounds and their use in the treatment of acute and/or chronic pain.

2. Background of the Invention

The study of compounds exerting their actions via the opioid receptor system has continued for nearly eight decades.[1] Though this has been a broad effort, the fundamental driving force for this endeavor relates to the elimination or reduction of the side-effect profile produced by the most frequently used or abused opiates morphine (1) and heroin (2). The wealth of knowledge accumulated in this time is enormous and includes examples of milestone discoveries commensurate with its breadth from the original concept of an opiate receptor[2] to the more recent cloning of three individual opioid receptor subtypes, mu[3-5] delta[6,7] and kappa.[8-10] Belonging to the superfamily of G protein-coupled receptors (GPCR), postulated to possess seven helical transmembrane (7TM) spanning regions, they are now known to be anatomically distributed in both the central and peripheral nervous systems and aside from modulation of pain are intimately involved in a diversity of biological events ranging from of the modulation of immune response[11] to hibernation.[12]

Over 100 million patients experience acute or chronic pain annually in the United States caused by headache, muscle strains and sprains, arthritis, trauma, cancer, surgery, and back injuries, among others. Because pain impairs one's ability to carry out a productive life, pain in general and chronic pain in particular are serious health and economic problems. Patients with advanced cancer pain, osteoarthritis, rheumatoid arthritis, or neuropathic pain frequently do not achieve adequate relief of pain with existing drugs owing to limited efficacy. Hence, there is a significant unmet medical need for safer orally-active and parenteral products for treating mild-moderate and moderate-severe pain. Market statistics show a continuing unmet medical need for safer, easier-to-use and more effective treatments for both acute and chronic pain.

U.S. Pat. No. 6,559,159 discloses a variety of N-substituted 4β-methyl-5-(3-hydroxyphenyl)morphans as opioid kappa receptor selective pure antagonists, and their use in a variety of end uses such as treatment of disease states that are ameliorated by binding of the kappa opioid receptor such as heroin or cocaine addictions, among other uses. (see also Thomas et al, *J. Med. Chem.*, 2002, 45, 3524-3530).

With the recent removal from the US market of various COX1 and COX2 mechanism based pain medications, there is a great need for new medications for treatment of acute and/or chronic pain, operating by different pathways so as to avoid the negative side effects of the withdrawn drugs. One potential pathway for pain treatment may be with the use of agonists for the opioid receptors, thus mimicking the pain alleviating aspects of the opiates, without the negative side effects of such illegal substances.

SUMMARY OF THE INVENTION

It is an object of the invention to provide compounds which act as opioid receptor agonists with high affinity.

It is another object of the invention to provide opioid receptor agonist compounds which bind to mu and delta opioid receptor subtypes.

It is another object of the invention to provide opioid receptor agonist compounds which provide relief of acute and/or chronic pain.

The objects of the present invention, and others, are accomplished with compounds represented by the formula (I):

wherein $R_1$ is $C_{1-8}$ alkyl, $C_{3-8}$ alkenyl, $C_{3-8}$ alkynyl, $C_{1-8}$ alkylaryl or one of the following groups:

or —$(CH_2)_n$(Het), wherein (Het) is a member selected from

R is hydrogen, $C_{1-8}$ alkyl, $C_{3-8}$ alkenyl, $C_{3-8}$ alkynyl, $C_{1-8}$ alkylaryl, —$CO_2R_8$;
$R_2$ is H, halogen, $C_{1-4}$ alkyl, CN or $OCH_3$;
Y is OH, $OR_9$, $C_{1-8}$ alkyl, F, Cl, Br, $CF_3$ or CN;
W is a member selected from the group consisting of: H, OH, —$CO_2R_8$; amino, —$NR_3SO_2R_7$, —$NR_3CO_2R_7$, —$CONH_2$; and —NHCHO
n is 1, 2, 3 or 4;
$R_3$ is hydrogen, $C_{1-8}$ alkyl, $C_{3-8}$ alkenyl, $C_{3-8}$ alkynyl, $C_{1-8}$ alkylaryl, —$CH_2Y$ or —$CO_2R$;
$R_4$ is hydrogen, $C_{1-8}$ alkyl, $C_{3-8}$ alkenyl, $C_{3-8}$ alkynyl, or $C_{1-8}$ alkylaryl;
$R_5$ and $R_6$ are each, independently, hydrogen, $C_{1-8}$ alkyl, $C_{3-8}$ alkenyl, $C_{3-8}$ alkynyl, or $C_{1-8}$ alkylaryl;
$R_7$ and $R_8$ are each independently, $C_{1-8}$ alkyl, $C_{3-8}$ alkenyl, $C_{3-8}$ alkynyl, or $C_{1-8}$ alkylaryl;

and the use of these compounds in pharmaceutical compositions and methods for the treatment of acute and/or chronic pain in subjects in need thereof.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The present invention provides opioid receptor agonists, which are useful in the treatment of pain, whether of the acute or chronic variety. Compounds of the present invention are represented by the formula (I):

wherein $R_1$ is $C_{1-8}$ alkyl, $C_{3-8}$ alkenyl, $C_{3-8}$ alkynyl, $C_{1-8}$ alkylaryl or one of the following groups:

or —$(CH_2)_n$(Het), wherein (Het) is a member selected from

R is hydrogen, $C_{1-8}$ alkyl, $C_{3-8}$ alkenyl, $C_{3-8}$ alkynyl, $C_{1-8}$ alkylaryl, —$CO_2R_8$;

$R_2$ is H, halogen, $C_{1-4}$ alkyl, CN or $OCH_3$;

Y is OH, $OR_9$, $C_{1-8}$ alkyl, F, Cl, Br, $CF_3$ or CN;

W is a member selected from the group consisting of: H, OH, —$CO_2R_8$; amino, —$NR_3SO_2R_7$, —$NR_3CO_2R_7$, —$CONH_2$; and —NHCHO n is 1, 2, 3 or 4;

$R_3$ is hydrogen, $C_{1-8}$ alkyl, $C_{3-8}$ alkenyl, $C_{3-8}$ alkynyl, $C_{1-8}$ alkylaryl, —$CH_2Y$ or —$CO_2R$;

$R_4$ is hydrogen, $C_{1-8}$ alkyl, $C_{3-8}$ alkenyl, $C_{3-8}$ alkynyl, or $C_{1-8}$ alkylaryl;

$R_5$ and $R_6$ are each, independently, hydrogen, $C_{1-8}$ alkyl, $C_{3-8}$ alkenyl, $C_{3-8}$ alkynyl, or $C_{1-8}$ alkylaryl;

$R_7$ and $R_8$ are each independently, $C_{1-8}$ alkyl, $C_{3-8}$ alkenyl, $C_{3-8}$ alkynyl, or $C_{1-8}$ alkylaryl.

Even more preferred are compounds of the above formula, wherein Y, W, n, $R_2$ and $R_8$ are as noted above;

$R_1$ is $C_{2-8}$ alkyl, $C_{3-8}$ alkenyl, or a group of the following formulae:

$R_3$ is hydrogen, or $C_{1-8}$ alkyl;

$R_4$ is hydrogen, or $C_{1-8}$ alkyl;

$R_5$ and $R_6$ are each independently, hydrogen, $C_{1-8}$ alkyl, or $C_{1-8}$ alkylaryl; and $R_7$ is $C_{1-8}$ alkyl, or $C_{1-8}$ alkylaryl.

Still more preferred are those compounds wherein Y, n, $R_2$ and $R_8$ are the same as noted above;

$R_1$ is $C_{2-8}$ alkyl, $C_{3-8}$ alkenyl, or a group selected from the following formulae:

W is OH or $CO_2R_8$;

$R_3$ is hydrogen, or $C_{1-4}$ alkyl;

$R_4$ is hydrogen or $C_{1-4}$ alkyl;

$R_5$ and $R_6$ are each independently, hydrogen, or $C_{1-4}$ alkyl; and $R_7$ is $C_{1-4}$ alkyl.

Particularly preferred compounds of the present invention are those of the above noted main formula, wherein Y, n, $R_2$, and $R_9$ are as noted above;

$R_1$ is $C_{2-8}$ alkyl, $C_{3-8}$ alkenyl, $C_{1-4}$ alkylaryl or a member selected from the following formulae:

W is OH or $CO_2R_8$;

$R_3$ is hydrogen, or methyl;

$R_4$ is hydrogen or methyl;

$R_5$ and $R_6$ are each independently, hydrogen, or $C_{1-4}$ alkyl; and $R_7$ is $C_{1-4}$ alkyl.

A most preferred compound of the present invention is compound (23) having the following structure (shown in two different structural depictions for ease of understanding):

(23)

The present inventors have found that compounds of Formula (I) bearing the amino based substituent on the bicycle group provides phenylmorphan compounds that are opioid agonists at the μ (mu) and 67 (delta) opioid receptor subtypes. Administration of compounds of the present invention can provide relief of acute and/or chronic pain As used throughout this disclosure, the terms "alkyl group" or "alkyl radical" encompass all structural isomers thereof, such as linear, branched and cyclic alkyl groups and moieties. Unless stated otherwise, all alkyl groups described herein may have 1 to 8 carbon atoms, inclusive of all specific values and subranges there between, such as 2, 3, 4, 5, 6, or 7 carbon atoms.

As used herein, the term "aralkyl group" refers to an aryl moiety bonded to an alkyl radical. The aryl moiety may have 6 to 20 carbon atoms. The aryl moiety may contain only carbon and hydrogen atoms. Alternatively, the aryl moiety may contain heteroatoms, for example 1, 2, or 3 heteroatoms (e.g., oxygen, nitrogen, and sulfur). A particularly preferred aryl moiety is phenyl-. The alkyl radical of the aralkyl group may be as described above. The alkyl group or moiety and/or the aryl moiety may be substituted. Suitable substituents include halogens (F, Cl, Br and I), alkyl groups (e.g., $C_1$-$C_8$), alkenyl groups (e.g., $C_2$-$C_8$), alkoxy groups (e.g., $C_1$-$C_8$ alkoxy groups), hydroxy, —$CF_3$, —CN, —$NH_2$, —$NHR_a$, or —$N(R_a)_2$. The $R_a$ groups are, independently, an alkyl group (such as described above), an aryl group (such as phenyl) or an aralkyl group group (such as benzyl). Alternatively, the $R_a$ groups may, together, form a cyclic alkyl group. Such a cyclic alkyl group may, preferably, contain 3 to 8 carbon atoms, with 4 or 5 carbon atoms particularly preferred.

The alkenyl group or alkynyl group may have one or more double or triple bonds, respectively. As will be readily appreciated, when an alkenyl or alkynyl group is bonded to a heteroatom a double or triple bond is not formed with the carbon atom bonded directly to the heteroatom.

The aryl group is a hydrocarbon aryl group, such as a phenyl, naphthyl, phenanthryl, anthracenyl group, which may have one or more $C_{1-4}$ alkyl group substituents. The aryl moiety of the aryl-$C_{1-8}$ alkyl group is preferably a phenyl group. The phenyl group may be unsubstituted or may be substituted with one or more of the substituents described above. The $C_{1-8}$ alkyl moiety of the aryl-$C_{1-8}$ alkyl group may be unsubstituted or substituted with one or more of the substituents described above or keto, i.e., 2 hydrogens on a carbon atom are replaced by =O. The substituent, when present, is preferably at the beta or gamma carbon atom and/or alpha to the aryl moiety.

The compounds of the present invention are opiate receptor agonists which are preferably selective for the mu and delta receptor subtypes.

Figure 1:
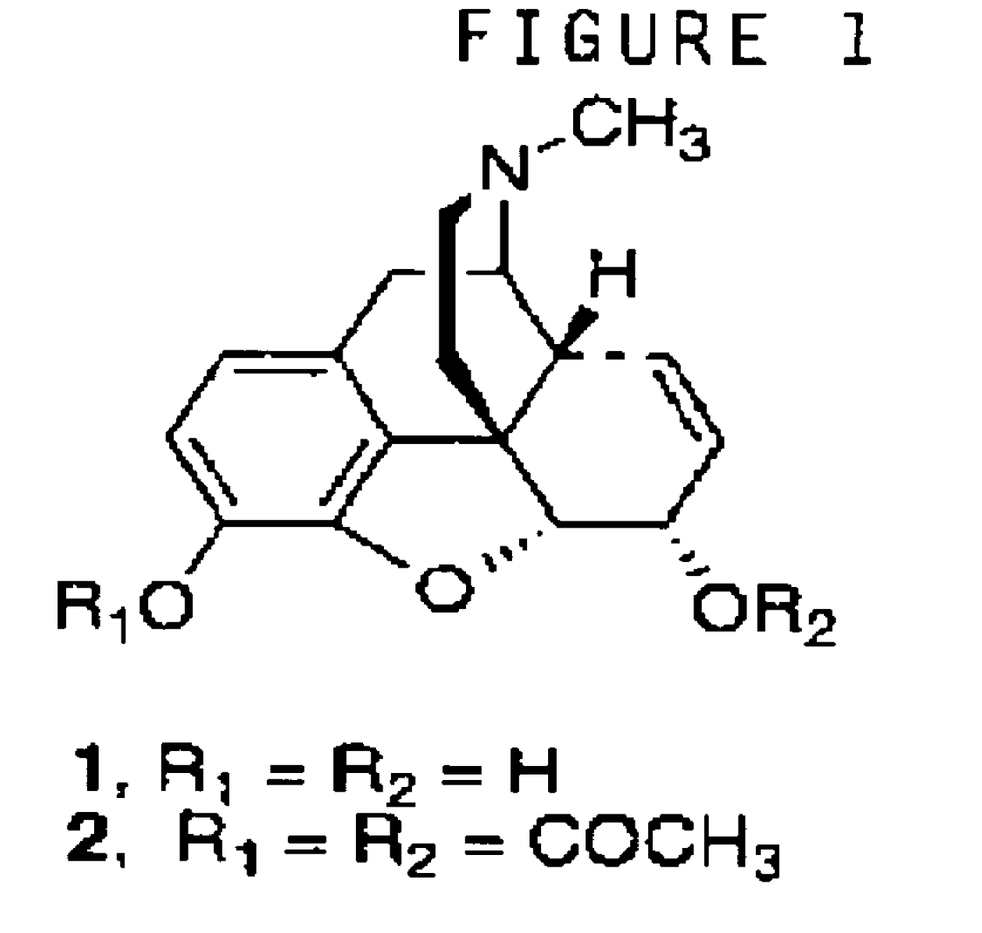
FIG. 1 shows a chemical structure of compounds (1) and (2)
Figure 2:
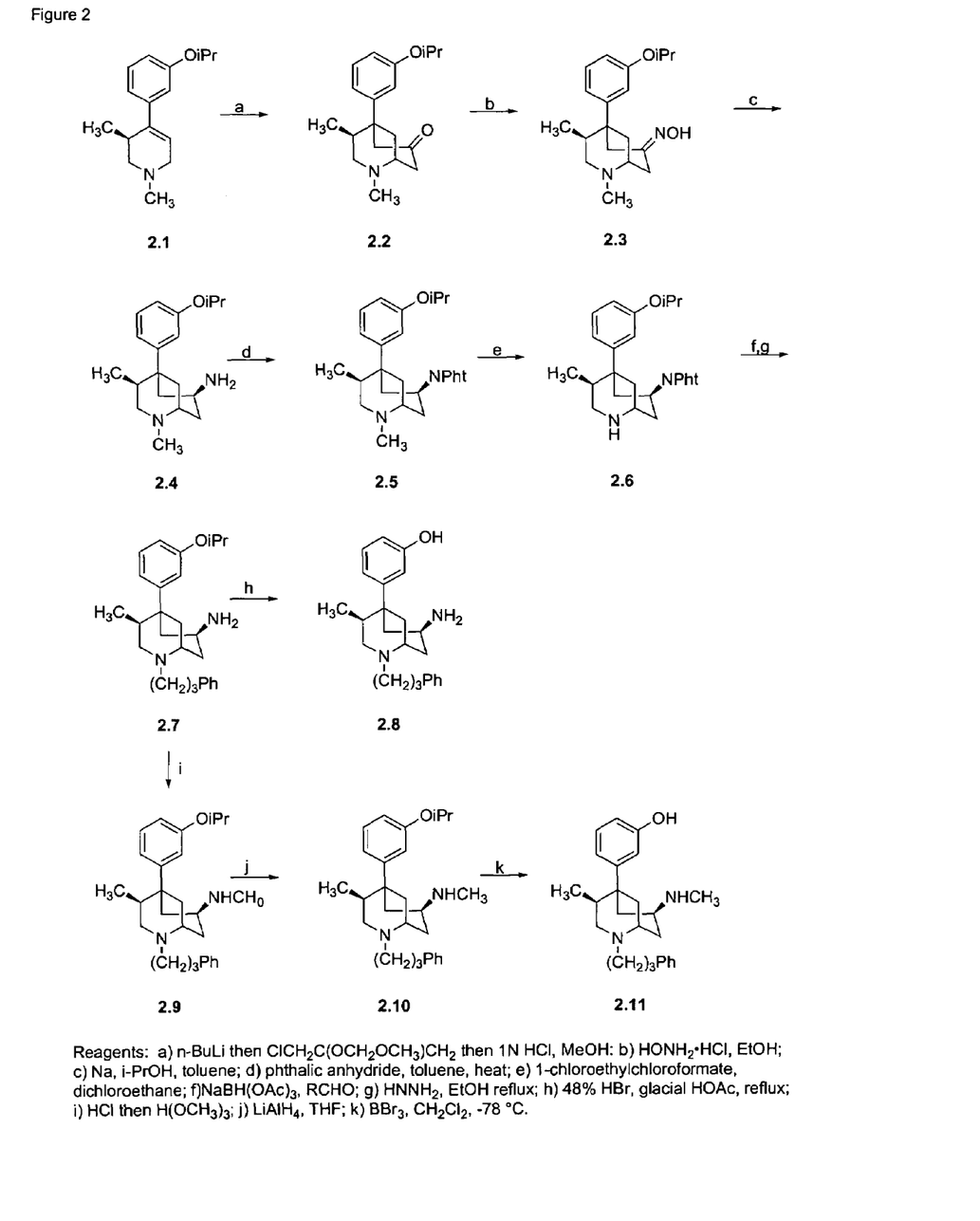
FIG. 2 provides an exemplary synthesis of illustrative compound 23.

The compounds of the present invention may be synthesized, for example, in accordance with the reaction sequence shown in FIG. 2. A specific synthetic sequence for an illustrative compound of the present invention, compound (23), is shown in FIG. 2.

The compounds of the present invention may be in the form of a pharmaceutically acceptable salt via amine protonation with a suitable acid. The acid may be an inorganic acid or an organic acid. Suitable acids include, for example, hydrochloric, hydroiodic, hydrobromic, sulfuric, phosphoric, citric, fumaric, acetic and formic acids.

The receptor selectivities discussed above are determined based on the binding affinities at the receptors indicated or in functional assays such as the [35S]GTP-γ-S assay.

The compounds of the present invention may be used to bind opioid receptors. Such binding may be accomplished by contacting the receptor with an effective amount of the inventive compound. Of course, such contacting is preferably conducted in a aqueous medium, preferably at physiologically relevant ionic strength, pH, etc.

The inventive compounds may also be used to treat patients having acute and/or chronic pain. These compounds are also useful to treat opiate addiction (such as heroin addiction), or cocaine addiction. The compounds of the present invention may also be used as antimigraine agents, as immunomodulators, as immunosuppressives, as antiarthritic agents, The compounds may be administered in an effective amount by any of the conventional techniques well-established in the medical field. For example, the compounds may be administered orally, intravenously, or intramuscularly. When so administered, the inventive compounds may be combined with any of the well-known pharmaceutical carriers and additives that are customarily used in such pharmaceutical compositions. For a discussion of dosing forms, carriers, additives, pharmacodynamics, etc., see Kirk-Othmer Encyclopedia of Chemical Technology, Fourth Edition, Vol. 18, 1996, pp. 480-590, incorporated herein by reference. The patient is preferably a mammal, with human patients especially preferred. Effective amounts are readily determined by those of ordinary skill in the art.

The compounds of the present invention can be administered as a single dosage per day, or as multiple dosages per day. When administered as multiple dosages, the dosages can be equal doses or doses of varying amount, based upon the time between the doses (i.e. when there will be a longer time between doses, such as overnight while sleeping, the dose administered will be higher to allow the compound to be present in the bloodstream of the patient for the longer period of time at effective levels). Preferably, the compound and compositions containing the compound are administered as a single dose or from 2-4 equal doses per day.

Suitable compositions containing the present compounds further comprise a physiologically acceptable carrier, such as water or conventional pharmaceutical solid carriers, and if desired, one or more buffers and other excipients.

EXAMPLES

Having generally described this invention, a further understanding can be obtained by reference to certain specific examples which are provided herein for purposes of illustration only and are not intended to be limiting unless otherwise specified.

Chemistry

Compounds were synthesized as shown in FIG. 2. Treatment of 2.1 with n-butyl lithium followed by the addition of Okahara's reagent followed by concomitant deprotection and cyclization gives the 7-oxo derivative 2.2 as a pure single enantiomer. Conversion of 2.2 to the oxime 2.3 followed by reduction with sodium and isopropanol gives the amino derivative 2.4. Treatment of 2.4 with phthalic anhydride gives the amino-protected compound 2.5, which, on demethylation with ACE-chloride, provides 2.6. Reductive amination of 2.6 with sodium triacetoxyborohydride using the hydrocinnamaldehyde followed by removal of the phthaloyl protecting group yields the N-phenpropyl compound 2.7. Treatment of 2.7 with 48% hydrobromic acid gives the target compound 2.8. Condensation of 2.7 with trimethyl-orthoformate provided the N-formyl compound 2.9. Reduction of 2.9 using lithium aluminum hydride in tetrahydrofuran afforded the N-methyl compound 2.10. Deprotection of the phenolic group was accomplished using boron tribromide to yield target compound 2.11.

Biological Activity

Measures of agonist/antagonist activity were obtained by monitoring the ability of the test compounds stimulate [$^{35}$S]GTP-γ-S binding produced by the selective agonists (D-Ala$^2$, MePhe$^4$,Gly-ol$^5$)enkephalin (DAMGO, mu receptor), D-Pen2,D-Pen5]-enkephalin (DPDPE, delta receptor) and inhibit U69.593 (kappa receptor) stimulation of [$^{35}$S]GTP-γ-S.

Determination of intrinsic activity. Test compounds 2.8 and 2.11 were assayed for their ability to stimulate [35S] GTP-γ-S binding in CHO cell membrane homogenates expressing either the human mu or human delta opioid receptor. The compounds were assayed in triplicate at eight different concentrations. DAMGO, a mu opioid receptor full agonist, and DPDPE, a delta opioid receptor full agonist, dose response curves were run for each experiment as positive controls for the appropriate receptor. The membranes were incubated with one of eight concentrations of positive control or test compound, 0.1 nM [35S]GTP-γ-S and 10 μM GDP in a 50 mM HEPES buffer (pH 7.4) at room temperature for one hour, after which bound radioligand was separated from free via rapid vacuum filtration over GF-B filters using a Brandel Scientific (Gaithersburg, MD) 96-well harvester. Bound radioactivity was determined using a TopCount 12-detector instrument (Packard Instruments) using standard scintillation counting techniques. The data were normalized to samples containing vehicle (basal binding), and a three-parameter logistic curve fit to the data using Prism (version 3.0, Graph-Pad Software, Inc., San Diego, Calif.). The EC50 and upper asymptote (Emax) were calculated for each compound and the data reported as mean ±SEM.

Determination of apparent affinity (Ke). The ability of a single concentration of test compound to shift the U69,593 (full kappa opioid receptor agonist) dose response curve to the right was used to determine the apparent affinity (Ke) of the test compounds. Assay conditions and analysis of the data were identical to that detailed for the determination of intrinsic activity except that membrane homogenates from CHO cells expressing the human kappa opioid receptor were used, and a single, identical concentration of test compound was included with each assayed concentration of kappa agonist. The EC50 values were calculated for the U69,593 (A) and U69,593+test compound (A') dose response curves, and these values used to calculate the test compound Ke value from the formula: Ke=[L]/(DR−1), where [L] equals the concentration of test compound in the assay and DR equals the dose ratio or A'/A.

Results

Figures 3, 3A, 3B:
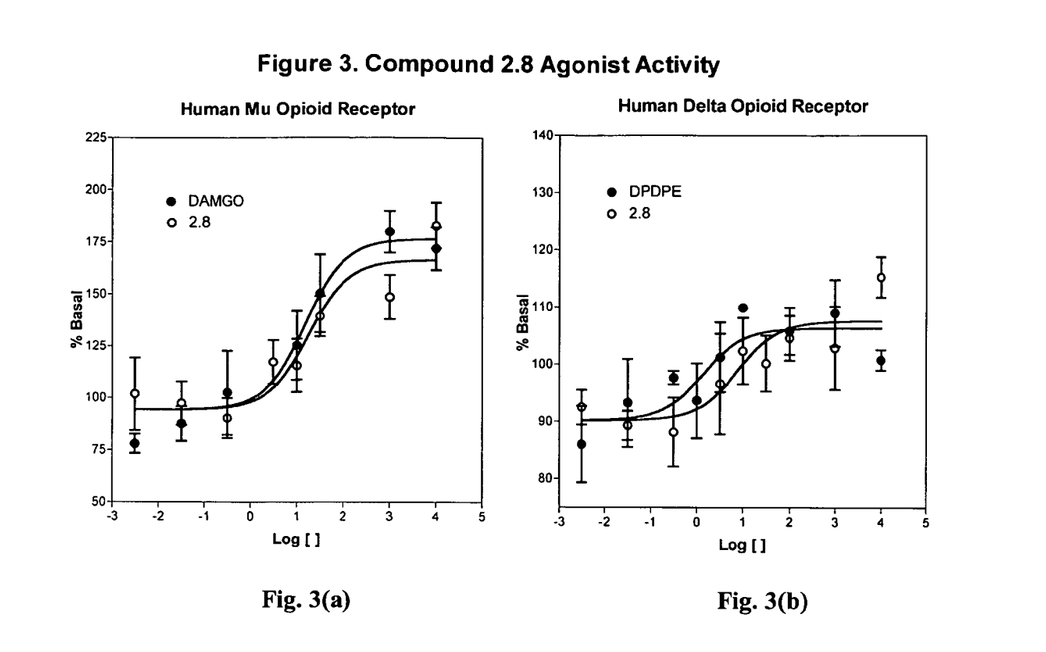
FIGS. 3(a) and 3(b) are graphical representations of the agonist activity of 2.8 at the human mu and delta opioid receptors, respectively.

FIGS. 3(a) and 3(b). Agonist Activity of 2.8.

These data are representative of at least three separate experiments run to determine the intrinsic activity of 2.8 at the human mu (FIG. 3(a)) and delta (FIG. 3(b)) opioid receptors. DAMGO, the mu agonist standard for this assay, and DPDPE, the delta agonist standard, stimulated [35S]GTP-γ-S binding in keeping with their known full agonist activity. Compound 2.8 was a partial agonist at the mu receptor since it failed to stimulate binding to the same level as DAMGO, and it-was a full agonist at the delta opioid receptor.

Figures 4, 4A, 4B:
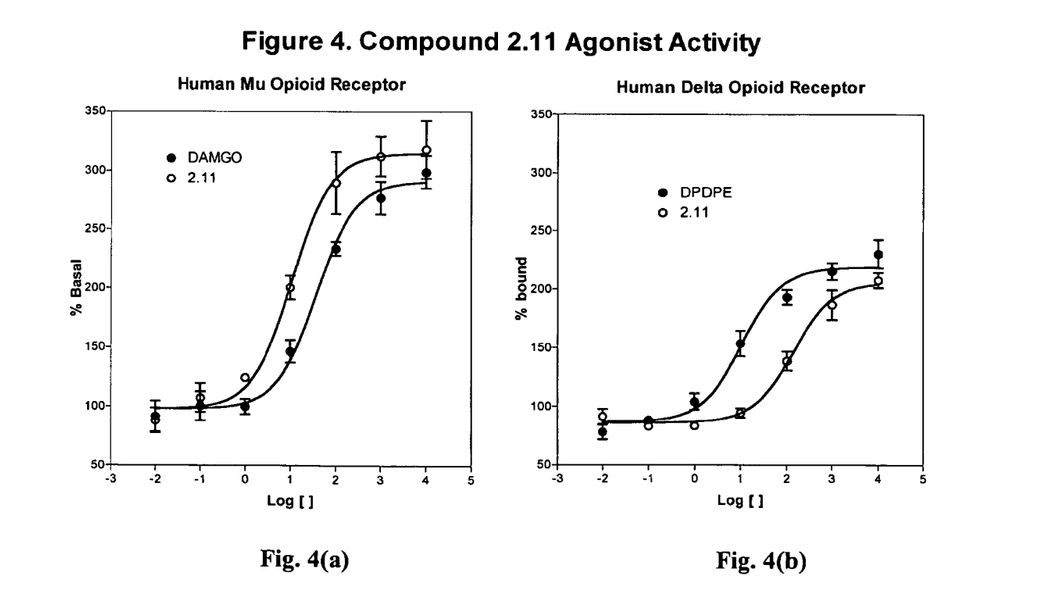
FIGS. 4(a) and 4(b) are graphical representations of the agonist activity of 2.11 at the human mu and delta opioid receptors, respectively.

FIGS. 4(a) and 4(b). Agonist Activity of 2.11.

These data are representative of at least three separate experiments run to determine the intrinsic activity of 2.11 at the human mu (FIG. 4(a)) and delta (FIG. 4(b)) opioid receptors. DPDPE, the agonist standard for this assay, stimulated [35S] GTP-γ-S binding in keeping with its known full agonist activity. Compound 2.11 was a full agonist at the mu opioid receptor, and a partial agonist at the delta opioid receptor.

Table 1. Summary of 2.8 and 2.11 Activity at Mu, Delta and Kappa Opioid receptors. The data represent the mean ±SEM from at least three separate experiments. The Emax values for 2.8 and 2.11 are reported relative to the Emax for either DAMGO (mu receptor) or DPDPE (delta receptor). The data indicate 2.8 is a partial agonist at the mu opioid receptor, a potent full agonist at the delta opioid receptor and a good inhibitor at the kappa opioid receptor. In contrast, compound 2.11 was a full agonist at the mu receptor, a partial agonist at the delta receptor and a good inhibitor of the kappa receptor. It should be noted that although the Emax for 2.11 is greater than that for DAMGO, a t-test indicated that the maximum stimulation of [35S]GTP-γ-S binding caused in the presence of 2.11 was not statistically different (p>0.05) than that caused by DAMGO.

TABLE 1

Data for Test Compound for Mu, Delta, and Kappa Opioid Receptor in Functional In Vitro Assays

| | Agonist | | | | Antagonist |
|---|---|---|---|---|---|
| | μ | | δ | | |
| Compound | $EC_{50}$ | Emax (% DAMGO) | $EC_{50}$ | Emax (% DPDPE) | κ $K_e$ |
| (2.8) | 19.5 ± 8.8 | 74 ± 12 | 7.45 ± 2.0 | 101 ± 14 | 10.1 ± 3.0 |
| 2.11 | 31.5 ± 11.8 | 105 ± 7 | 98.3 ± 23.5 | 79.7 ± 7.7 | 3.8 ± 7.3 |

Experimental Section

Melting points were determined on a Thomas-Hoover capillary tube apparatus and are not corrected. Elemental analyses were obtained by Atlantic Microlabs, Inc. and are within ±0.4% of the calculated values. All optical rotations were determined at the sodium D line using a Rudolph Research Autopol III polarimeter (1-dm cell). $^1$H NMR were determined on a Bruker WM-250 spectrometer using tetramethylsilane as an internal standard. Silica gel 60 (230-400 mesh) was used for all column chromatography. All reactions were followed by thin-layer chromatography using Whatman silica gel 60 TLC plates and were visualized by UV or by charring using 5% phosphomolybdic acid in ethanol. All solvents were reagent grade. Tetrahydrofuran and diethyl ether were dried over sodium benzophenone ketyl and distilled prior to use.

[$^{35}$S]GTP-γ-S (SA=1250 Ci/mmol) were obtained from DuPont New England Nuclear (Boston, Mass.). U69,593 was obtained from Research Biochemicals International (Natick, Mass.). Levallorphan was a generous gift from Kenner Rice, Ph.D., NIDDK, NIH (Bethesda, Md.). GTP-γ-S and GDP were obtained from Sigma Chemical Company (St. Louis, Mo.). The sources of other reagents are published. (CAUTION: Read reference 35 and references cited therein for information on N-methyl-4-phenyl-1,2,3,6-tetrahydropyridine, MPTP and its derivatives).

(−)-(1R,4S,5S)-5-[3-(1-methylethoxy)phenyl]-2,4-di-methyl-2-azabicyclo[3.3.1]nonan-7-one (2.2): To a solution of (S)-1,2,3,6-tetrahydro-1,3-dimethyl-4-[3-(1-methylethoxy)phenyl]pyridine (2.1) (1 eq) dissolved in THF (20 mL/g) and cooled to −10° C. was added n-butyl lithium (1.6M in hexanes) slowly until a red color is maintained followed by an addition of 1.1 eq. This material is stirred for 1 h at 10° C. and then cannulated quickly into a solution of Okahara's reagent (distilled to high purity) in THF (15 mL/g, 1.1 eq) at −78° C. followed by stirring for 2 h. The temperature should be kept below −30° C. during cannulation. This material is then poured into 2N HCl and extracted twice with ethyl ether. The aqueous layer is allowed to stand for 15 min followed by addition of 50% NAOH to pH 14 and extraction (3×) with ethyl ether. The ether is then washed (1N NaOH, $H_2O$) and the solvent removed under vacuum. The resulting residue of product and water is dissolved in MeOH (30 mL/g) and nitrogen is bubbled through the solution for 5 min. To this is added concentrated HCl (2 mL/g), and the mixture is allowed to stand at room temperature until the reaction is complete as indicated by TLC (TLC condition: $SiO_2$; elution with 50% (80% $CHCl_3$:18% $CH_3OH$:2% $NH_4OH$) in $CHCl_3$. Detection: 5% phosphomolybdic acid in ethanol. To this mixture was added 50% NaOH to adjust the pH to ~10 and the methanol is removed under aspirator vacuum. The aqueous residue is then extracted several times with 3:1 (methylene chloride: THF). The organic extracts are combined and washed twice with water and once with brine, dried over sodium sulfate and evaporated to an oil. This material was purified by flash chromatography on silica gel using 25-50% (80% $CHCl_3$:18% $CH_3OH$:2% $NH_4OH$) in $CHCl_3$ to give 2.2 in 70% yield from 2.1. $^1$H NMR 7.24 (t,1,J=7.5 Hz), 6.77 (m, 3), 4.55 (m, 1), 3.49 (s, 1), 2.91 (dd,2,J=17 Hz and 16.5 Hz), 2.60 (m, 2), 2.35 (m, 5), 2.05 (m, 3), 1.35 (m, 6), 0.78 (d,3,J=6.8 Hz).

5-(3-Isopropoxy-phenyl)-2,4-dimethyl-2-aza-bicyclo [3.3.1]nonan-7-one oxime (2.3). 5-(3-Isopropoxy-phenyl)-2,4-dimethyl-2-aza-bicyclo[3.3.1]nonan-7-one (2.2) (3.11 g, 13.0 mmole) and hydroxylamine hydrochloride (4.50 g, 64.8 mmol) in EtOH (absolute, 195 mL) were heated to reflux for 3 h. The reaction mixture was allowed to cool to room temperature and the ethanol was removed under reduced pressure. The crude oil was dissolved in 2 N NaOH (100 mL) and extracted with 3:1 $CH_2Cl_2$/THF (4×50 mL). The combined organic layers were dried ($Na_2SO_4$), filtered, and concentrated under reduced pressure yielding crude product. The crude product was purified by flash chromatography (neutral alumina, Brockman activity II-III) eluting with 9:1 ethyl acetate:hexane to afford the title compound (3.6 g, 88%) as an off white solid. $^1$H NMR ($CDCl_3$) δ 8.47 (br, 1H), 7.23 (t, J=7.8 Hz, 1H), 7.00-6.72 (m, 3H), 4.54 (m, 1H), 3.63 (d, J=17 Hz, 1H), 3.29 (br, 1H), 2.94-2.85 (m, 2H), 2.51 (d, J=15.9 Hz, 1H), 2.44-2.40 (m, 4H), 2.05-1.87 (m, 5H), 1.33 (d, J=6.0 Hz, 6H), 0.76 (d, J=6.9 Hz, 3H).

5-(3-Isopropoxyphenyl)-2,4-dimethyl-2-aza-bicyclo [3.3.1]non on-7-ylamine (2.4). 5-(3-Isopropoxy-phenyl)-2,4-dimethyl-2-aza-bicyclo[3.3.1]nonan-7-one oxime (2.3) (4.87 g, 15.4 mmole) in dry isopropanol was added dropwise over 1 h. to a refluxing solution of dry toluene (450 mL) and Na (51.3 g, 2.23 mol). After complete addition of the oxime, two portions of isopropanol (250 mL) were added dropwise over 30 min. The reaction mixture was heated to reflux until all sodium was consumed followed by cooling to 50° C. and quenching with the careful addition of water (750 mL). The toluene layer was separated and the aqueous layer extracted with $CHCl_3$ (4×500 mL). The combined organic layers were dried dried ($Na_2SO_4$), filtered, and concentrated under reduced pressure yielding crude product. The crude product was purified by flash chromatography (neutral alumina, Brockman activity II-III) eluting with 9:1 ethyl acetate:ethanol to afford the title compound (4.42 g, 95%) as an off white solid. $^1$H NMR ($CDCl_3$) δ 7.23 (t, 1H, J=7.8), 7.00-6.72 (m, 3H), 4.52 (sept., 1H, J=6.1 Hz), 3.51 (m, 1H), 3.15 (m, 1H), 2.96 (m, 1H), 2.62 (m, 1H), 2.45-2.32 (m, 4H), 2.23 (s, 1H), 2.11 (m, 1H), 1.67 (m, 2H), 1.31 (d, 6H, J=6.0 Hz), 1.15 (m, 1H), 0.94 (m, 1H), 0.73 (d, 3H, J=6.9 Hz).

2-[5-(3-Isopropoxyphenyl)-2,4-dimethyl-2-aza-bicyclo [3.3.1]non-7-yl]-isoindole-1,3-dione (2.5). 5-(3-Isopropoxyphenyl)-2,4-dimethyl-2-aza-bicyclo[3.3.1]non-7-ylamine (2.4) (1.69 g, 5.6 mmol) was dissolved in toluene followed by the addition of phthalic anhydride (2.5 g, 16.8 mmol) and the reaction mixture was refluxed with a Dean-Stark trap overnight. The solution was then cooled, diluted with ethyl acetate, and filtered into a separatory funnel. The organic layer was washed with 1 N NaOH (3×30 ml) and water. The organic layer was collected, dried (Na$_2$SO$_4$) and the solvent removed under reduced pressure yielding crude product. The crude product was purified by filtering through a short column of neutral alumina (Brockman activity II-III) eluting with ethyl acetate to afford the title compound (1.50 g, 62%) as an off white solid. $^1$H NMR (CDCl$_3$) δ: 7.76 (m, 2H), 7.65 (m, 2H), 7.23 (t, 1H, J=7.8), 7.00-6.72 (m, 3H), 5.08 (m, 1H), 4.52 (sept., 1H, J=6.1 Hz), 3.15 (m, 1H), 2.96 (m, 1H), 2.62 (m, 1H), 2.45-2.32 (m, 4H), 2.23 (s, 1H), 2.11 (m, 1H), 1.67 (m, 2H), 1.31 (d, 6H, J=6.0 Hz), 1.15 (m, 1H), 0.94 (m, 1H), 0.73 (d, 3H, J=6.9 Hz).

2-[5-(3-Isopropoxy-phenyl)-4-methyl-2-aza-bicyclo[3.3.1]non-7-yl]-isoindole-1,3-dione (2.6). 2-[5-(3-Isopropoxyphenyl)-2,4-dimethyl-2-aza-bicyclo[3.3.1]non-7-yl]-isoindole-1,3-dione (2.5) (1.50 g, 3.5 mmol) was dissolved in dichloroethane and heated to reflux followed by the addition of 1-chloroethyl chloroformate (0.410 ml, 3.8 mmol). This solution was allowed to reflux for 3.5 hrs. The reaction was cooled and the solvent removed under reduced pressure. The crude material was taken up in ethyl acetate and washed with a saturated sodium bicarbonate solution (3×30 ml). The organic layer was collected, dried (Na$_2$SO$_4$) and the solvent removed under reduced pressure yielding crude product. This material was dissolved in methanol and refluxed overnight. The methanol was removed and the crude product dissolved in 1 N NaOH. The aqueous was extracted with 3:1 CH$_2$Cl$_2$:THF. The combined organic layers were collected, dried (Na$_2$SO$_4$) and the solvent removed under reduced pressure yielding crude product. This product was used with out further purification.

2-[5-(3-Isopropoxy-phenyl)-4-methyl-2-(3-phenyl-propyl)-2-aza-bicyclo[3.3.1]non-7-yl]-isoindole-1,3-dione. 2-[5-(3-Isopropoxy-phenyl)-4-methyl-2-aza-bicyclo[3.3.1]non-7-yl]-isoindole-1,3-dione (2.92 g, 7.0 mmol) and hydrocinamaldehyde (1.12 g, 8.3 mmol) were dissolved in dichloroethane (115 ml) followed by the addition of sodium triacetoxyborohydride (2.1 g, 9.7 mmol) and allowed to react at room temperature overnight. The reaction was quenched with the addition of a saturated sodium bicarbonate solution (200 ml) and the organic layer separated. The aqueous was then extracted with CHCl$_3$. The combined organic fractions were dried (NaSO4), filtered, and concentrated in vaccu. The crude product was then purified by flash chromatography on an aluminum oxide (neutral, Brockman activity II-III) column and eluting with 8:2 hexane:ethyl acetate giving 3.16 g (83.9%) of the desired product. $^1$H NMR (CDCl$_3$) δ 7.75 (m, 2H), 7.64 (m, 2H), 7.25 (m, 5H), 6.79 (m, 2H), 6.68 (d, J=7.8, 1H), 5.15 (m, 1H), 4.52 (sept., J=6.0 Hz, 1H), 3.27 (br, 1H), 3.08 (dd, J$_1$=6 Hz, J$_2$=3 Hz, 1H), 2.78-2.52 (m, 6H), 2.25-2.16 (m, 5H), 1.96-1.78 (m, 4H), 1.31 (d, J=6, 6H), 0.78 (d J=6.9, 3H).

5-(3-Isopropoxy-phenyl)-4-methyl-2-(3-phenyl-propyl)-2-aza-bicyclo[3.3.1] non-7-ylamine (2.7). 2-[5-(3-Isopropoxy-phenyl)-4-methyl-2-(3-phenyl-propyl)-2-aza-bicyclo[3.3.1]non-7-yl]-isoindole-1,3-dione (3.16 g, 7.8 mmol) and hydrazine (1.4 g, 43,7 mmol) were dissolved in ethanol (150 ml) and refluxed overnight. The solution was then cooled and the white percipitate was filtered and washed with cold ethanol. The solution was concentrated in vacuu and the crude material taken up in 3;1 CH$_2$Cl$_2$:THF. The resulting white percipitate was filtered and washed with cold CH$_2$Cl$_2$. The organic layer was concentrated to yield 3.07 g (97%) of the desired product as a yellow soild. 1H NMR (CDCl$_3$) 7.18 (m, 6H), 6.71 (m, 3H), 4.56 (sept., J=6, 1H), 3.51 (m, 1H), 3.19 (br, 1H), 2.82 (m, 1H), 2.66 (m, 3H), 2.50 (m, 2H), 2.34 (m, 3H), 2.11 (m, 1H), 1.82 (m, 2H), 1.80 (m, 1H), 1.29 (d, J=6 Hz, 6H), 0.90 (m, 2H), 0.71 (d, J=7.2, 3H).

(−)-3-[(1 R,4S,5S,7R)-7-Amino-4-methyl-2-(3-phenyl-propyl)-2-aza-bicyclo[3.3.1 ] non-5-yl]phenol (2.8). 7-amino-4-methyl-5-(3-isopropoxyphenyl)-2-(3-phenylpropyl)-2-aza-bicyclo[3.3.1]nonane (2.7) (3.07 g, 7.8 mmole) was dissolved in glacial acetic acid (20 mL), 48% HBr (32.5 ml) was added, and the solution was heated to reflux for 15 h. The reaction mixture was allowed to cool to room temperature, poured into ice (100 g), and the pH was raised to 10 with 50% NaOH. The aqueous layer was extracted with 3:1 CH$_2$Cl$_2$:THF (3×100 mL). The combined organic extracts were dried (Na$_2$SO$_4$), filtered, and concentrated in vacuu. The crude product was purified by flash chromatography using silica gel and eluted with 65:35 CH$_2$Cl$_2$:CMA-80 to yield 2.8 g (88.3%) of the desired product as an off-white solid. The analytical sample was prepared by dissolving the free base in CHCl$_3$, acidifying with HCl in ether, and precipitated with ether. The ether/CHCl$_3$ mixture was decanted and the percipitate taken up in MeOH. The product was then precipitated out of the MeOH with ether. The solvent was decanted and the resultant material was dried under vacuum at 50° C. overnight. [α]$_D^{20}$=−20.5 (c 1.03, MeOH). $^1$H NMR (CDC13) δ 7.27-7.07 (m, 6H), 6.65-6.58 (m, 3H), 4.33 (br, 2H), 3.54 (br, 1H), 2.79 (m, 1H), 2.66-2.53 (m, 3H), 2.46 (t, J=7.0 Hz, 2H,), 2.31 (m, 3H), 2.04 (br, 1H), 1.77 (t, J=7.2, 2H), 1.53 (m, 1H), 1.14 (m, 1H), 0.98 (m, 1H), 0.70 (d, J=6.9 Hz, 3H,). $^{13}$C NMR (CD$_3$OD) δ 159.5, 149.3, 141.9, 131.4, 130.1, 129.9, 127.9, 117.5, 115.1, 114.9, 113.6, 113.4, 89.9, 57.1, 56.2, 55.8, 55.1, 51.4, 46.8, 45.0, 44.1, 40.1, 38.4, 37.4, 34.0, 30.6, 28.4, 27.4, 18.5. Anal. (C$_{24}$H$_{34}$Cl$_2$N$_2$O.H$_2$O) C, H, N.

7-Formylamino-5-(3-isopropoxyphenyl-4-methyl-2-(3-phenprop-1-yl)-2-aza-bicyclo[3.3.1)nononane (2.9). To a solution of 7-amino-5-(3-isopropoxyphenyl)-4-methyl-2-(3-phenprop-1-yl)-2-azabicyclo[3.3.1.]nononane (2.7, 115 mg, 0.28 mmol) in MeOH (1 mL) was added 1.0 M HCl in Et$_2$O (5 mL, 5 mmol). The solvent was removed under vacuum, and the residue suspended in trimethyl orthoformate (5 mL). The suspension was heated to reflux of 90 min, until the solids had completely dissolved. The reaction was then cooled to room temperature, and the solvant removed under vacuum. The residue was subjected to aqueous workup and chromatography as per Method 1 above to yield 82 mg (67%) of 2.9 as a clear oil. R$_f$ 0.3 (silica gel, 90:9:1 CHCl$_3$:MeOH:aqueous MeNH$_2$); $^1$H NMR (CDCl$_3$): δ 8.05 (s, 1H), 7.30-7.15 (m, 6H), 6.74-6.70 (m, 3H), 5.16 (d, 1H), 4.78 (m, 1H), 4.53 (m, 1H), 3.20 (b, 1H), 3.02 (dd, 1H), 2.74-2.62 (m,3H), 2.56-2.38 (m, 5H), 2.22-2.18 (m, 1H), 1.78 (quint, 2H), 1.61 (d, 1H), 1.32 (d, 6H), 1.24 (t, 1H), 0.98 (td, 1H), 0.74 (d, 3H).

5-(3-Isopropoxyphenyl)-4-methyl-7-methylamino-2-(3-phenprop-1 -yl)-2-azabicyclo[3.3.1]nononane (2.10). To a solution of 7-formylamino-5-(3-isopropoxyphenyl-4-methyl-2-(3-phenprop-1-yl)-2-azabicyclo[3.3.1)nononane (2.9, R=H, 110 mg, 0.25 mmol) in dry THF (8 mL) was added lithium aluminum hydride (120 mg, 3.2 mmol). The suspension was heated to reflux for 2 h, then cooled to room temperature and stirred an additional 14 h. The reaction was diluted with EtOAc (20 mL) and stirred for 20 min, then quenched with aqueous NaOH (1.0 M, 6 mL). The suspension was stirred vigorously for 10 min, then filtered through Celite and the solids rinsed with EtOAc (20 mL). The solvent was removed under vacuum to yield a yellow oil which was subjected to PTLC (20×20 cm×1 mm) on alumina with 98:1.8:0.2 CHCl$_3$:MeOH:aqueous MeNH$_2$. Product-containing substrate was scraped and eluted with EtOAc/EtOH, and the filtrate evaporated to yield 68 mg (64%) of 2.10 as a pale yellow oil: R$_f$ 0.3-0.4 (alumina, 98:1.8:0.2 CHCl$_3$:MeOH: aqueous MeNH$_2$); $^1$H NMR (CDCl$_3$): δ 7.30-7.15 (m, 6H), 6.81-6.69 (m, 3H), 4.53 (quint, 1H), 3.24-3.17 (m, 2H), 2.90 (dd, 1H), 2.68-2.63 (m, 3H), 2.49 (t, 2H), 2.43-2.34 (m, 6H), 2.12 (t, 1H), 1.79 (quint, 2H), 1.78 (d, 1H), 1.33 (d, 6H), 1.17 (t, 1H), 0.97 (m, 1H), 0.74 (d, 3H).

5-(3-Hydroxyphenyl)-4-methyl-7-methylamino-2-(3-phenylprop-1 -yl)-2-azabicyclo[3.3.1]nononane (2.11). The solution of 5-(3-Isopropoxyphenyl)-4-methyl-7-methylamino-2-(3-phenprop-1-yl)-2-azabicyclo[3.3.1]nononane (2.10, 90 mg, 0.21 mmol) was dissolved in $CH_2Cl_2$ (5 mL) and cooled to −78° C. A 1.0 M solution of boron tribromide in $CH_2Cl_2$ (1.0 mL, 1.0 mmol) was added slowly, and the resulting suspension stirred at −78° C. for 15 min. Water (2 mL) was then added, and the solvent removed under vacuum. The resulting brown, gummy solid was dissolved in acetone (10 mL), and conc. aq. HCl (10 mL). The acetone was removed under vacuum, and the remaining aqueous solution was extracted with EtOAc (10 mL). The aqueous solution was then neutralized (pH ~4) with 10% aqueous NaOH, and made basic (pH ~9) with solid $Na_2CO_3$. The aqueous solution was extracted with EtOAc (2×50 mL), then the combined extracts were dried over $Na_2SO_4$, filtered, and evaporated to yield a yellow residue. The residue was subjected to PTLC (20×20 cm×1 mm) on alumina with 95:4.5:0.5 $CHCl_3$:MeOH:aqueous $MeNH_2$. Product-containing substrate was scraped and eluted with EtOH, and the filtrate evaporated to yield 60 mg (74%) of 2.11 as a colorless, slightly cloudy oil: $R_f$ 0.3 (alumina, 95:4.5:0.5 $CHCl_3$:MeOH:aqueous $MeNH_2$); $^1$H NMR $CDCl_3$): δ 7.29-7.07 (m, 6H), 6.65-6.59 (m, 3H), 6.0-5.2 (b, 2H, exch.), 3.32 (m, 1H), 3.15 (b, 1H), 2.81 (dd, 1H), 2.66-2.60 (m, 8H), 2.49-2.27 (m, 1H), 2.05-1.99 (m, 1H), 1.78 (quint, 2H), 1.51 (d, 1H), 0.99 (m, 1H) 0.86 (m, 1H), 0.68 (d, 3H). $^{13}$C NMR ($CDCl_3$): δ 157.21, 151.55, 142.59, 129.45, 128.70, 128.47, 125.88, 116.57, 113.20, 55.91, 54.68, 54.53, 53.54, 46.62, 40.19, 37.97, 33.61, 32.80, 31.25, 29.90, 29.35, 18.75. Anal. of hydrochloride salt ($C_{25}H_{36}Cl_2N_2O\cdot H_2O$) C,H,N.

REFERENCES (1) Aldrich, J. V. Analgesics. In *Burger's Medicinal Chemistry and Drug Discovery*, Wolff, M. E. Eds.; John Wiley & Sons: New York, 1996; Vol. 3.

(2) Pert, C. B.; Snyder, S. H. Opiate receptor: Demonstration in nervous tissue. *Science* 1973,179, 1011-1014.

(3) Chen, Y.; Mestek, A.; Liu, J.; Hurley, J. A.; Yu, L. Molecular cloning and functional expression of a μ-opioid receptor from rat brain. *Mol. Pharmacol.* 1993, 44, 8-12.

(4) Thompson, R. C.; Mansour, A.; Akil, H.; Watson, S. J. Cloning and pharmacological characterization of a rat mu opioid receptor. *Neuron* 1993, 11(5), 903-13.

(5) Wang, J. B.; Johnson, P. S.; Persico, A. M.; Hawkins, A. L.; Griffin, C. A.; Uhl, G. R. Human μ opiate receptor: cDNA and genomic clones, pharmacological characterization and chromosomal assignment. *FEBS Lett.* 1994, 338, 217-222.

(6) Keiffer, B. L.; Befort, K.; Gaveriaux-Ruff, C.; Hirth, C. G. The δ-opioid receptor: Isolation of a cDNA by expression cloning and pharmacological characterization. *Proc. Natl Acad. Sci. U.S.A.* 1992, 89,12048-12052.

(7) Evans, C. J.; Keith, D. E., Jr.; Morrison, H.; Magendzo, K.; Edwards, R. H. Cloning of a delta opioid receptor by functional expression. *Science* 1992, 258, 1952-1955.

(8) Meng, F.; Xie, G. X.; Thompson, R. C.; Mansour, A.; Goldstein, A.; Watson, S. J.; Akil, H. Cloning and pharmacological characterization of a rat kappa opioid receptor. *Proc Natl Acad Sci USA* 1993, 90(21), 9954-8.

(9) Minami, M.; Toya, T.; Katao, Y.; Maekawa, K.; Nakamura, S.; Onogi, T.; Kaneko, S.; Satoh, M. Cloning and expression of a cDNA for the rat kappa-opioid receptor. *FEBS Lett* 1993, 329(3), 291-5.

(10) Nishi, M.; Takeshima, H.; Fukuda, K.; Kato, S.; Mori, K. cDNA cloning and pharmacological characterization of an opioid receptor with high affinities for kappa-subtype-selective ligands. *FEBS Lett* 1993, 330(1), 77-80.

(11) Nunez, G.; Urzua, J. [Opioids and the immune system]. *Rev Med Chil* 1999, 127(3), 341-8.

(12) Bruce, D. S.; Bailey, E. C.; Setran, D. P.; Tramell, M. S.; Jacobson, D.; Oeltgen, P. R.; Horton, N. D.; Hellgren, E. C. Circannual variations in bear plasma albumin and its opioid-like effects on guinea pig ileum. *Pharmacol Biochem Behav* 1996, 53(4), 885-9.

(13) Volpicelli, J. R.; Alterman, A. I.; Hayashida, M.; O'Brien, C. P. Naltrexone in the treatment of alcohol dependence. *Arch. Gen. Psychiatry* 1992, 49, 876-879.

(14) Volpicelli, J. R.; Watson, N. T.; King, A. C.; Sherman, C. E.; O'Brien, C. P. Effect of naltrexone on alcohol "high" in alcoholics. *Am. J. Psychiatry* 1995,152, 613-615.

(15) Marki, A.; Monory, K.; Otvos, F.; Toth, G.; Krassnig, R.; Schmidhammer, H.; Traynor, J. R.; Roques, B. P.; Maldonado, R.; Borsodi, A. Mu-opioid receptor specific antagonist cyprodime: characterization by in vitro radioligand and [35S]GTPgammaS binding assays. *Eur J Pharmacol* 1999, 383(2), 209-14.

(16) Portoghese, P. S. The design of 5-selective opioid receptor antagonists. *Il Farmaco* 1993, 48(2), 243-251.

(17) Portoghese, P. S.; Lipkowski, A. W.; Takemori, A. E. Binaltorphimine and nor-binaltorphimine, potent and selective κ-opioid receptor antagonists. *Life Sci.* 1987, 40(13), 1287-1292.

(18) Olmsted, S. L.; Takemori, A. E.; Portoghese, P. S. A remarkable change of opioid receptor selectivity on the attachment of a peptidomimetic κ address element to the δ antagonist, natrindole: 5'-[$N^2$-alkylamidino)methyl]naltrindole derivatives as a novel class of κ opioid receptor antagonists. *J. Med. Chem.* 1993, 36(1),179-180.

(19) Jones, R. M.; Hjorth, S. A.; Schwartz, T. W.; Portoghese, P. S. Mutational evidence for a common kappa antagonist binding pocket in the wild-type kappa and mutant mu[K303E] opioid receptors. *J Med Chem* 1998, 41(25), 4911-4.

(20) Schwyzer, R. ACTH: A short introductory review. *Ann. N.Y. Acad. Sci.* 1977, 247, 3-26.

(21) Trujillo, K. A.; Akil, H. Changes in prodynorphin peptide content following treatment with morphine or amphetamine: possible role in mechanisms of action of drug of abuse. *NIDA Res Monogr* 1989, 95, 550-1.

(22) Smiley, P. L.; Johnson, M.; Bush, L.; Gibb, J. W.; Hanson, G. R. Effects of cocaine on extrapyramidal and limbic dynorphin systems. *J Pharmacol Exp Ther* 1990, 253(3), 938-43.

(23) Corbett, A. D.; Paterson, S. J.; McKnight, A. T.; Magnan, J.; Kosterlitz, H. W. Dynorphin and dynorphin are ligands for the kappa-subtype of opiate receptor. *Nature* 1982, 299(5878), 79-81.

(24) Spanagel, R.; Herz, A.; Shippinberg, T. A. Opposing tonically active endogenous opioid systems modulate the mesolimbic dopaminergic pathway. *Proc. Natl. Acad. Sci. U.S.A.* 1992, 89, 2046-2050.

(25) Spanagel, R.; Shippenberg, T. S. Modulation of morphine-induced sensitization by endogenous K opioid systems in the rat. *Neurosci. Lett.* 1993, 153, 232-236.

(26) Zadina, J. E.; Hackler, L.; Ge, L.-J.; Kastin, A. J. A potent and selective endogenous agonist for the μ-opiate receptor. *Nature* 1997, 386, 499-502.

(27) Zimmerman, D. M.; Nickander, R.; Homg, J. S.; Wong, D. T. New structural concepts for narcotic antagonists defined in a 4-phenylpiperidine series. *Nature* 1978, 275, 332-334.

(28) Zimmerman, D. M.; Smits, S.; Nickander, R. Further investigation of novel 3-methyl-4-phenylpiperidine narcotic antagonists. In *Proceedings of the 40th Annual Scientific Meeting of the Committee on Problems of Drug Dependence,* 1978, pp. 237-247.

(29) Zimmerman, D. M.; Smits, S. E.; Hynes, M. D.; Cantrell, B. E.; Reamer, M.; Nickander Structural requirements for affinity and intrinsic activity at the opiate receptor defined in 4-phenylpiperidine and related series. In *Problems of Drug Dependence* 1981, *Proceedings of the 43rd Annual Scientific Meeting of the Committee on Problems of Drug Dependence, Inc.*, Harris, L. S. Eds.; 1981, pp. 112-116.

(30) Zimmerman, D. M.; Smits, S. E.; Hynes, M. D.; Cantrell, B. E.; Reamer, M.; Nickander, R. Structural requirements for affinity and intrinsic activity at the opiate receptor defined in 4-phenylpiperidine and related series. In *Problems of Drug Dependence*, 1981, *Proceedings of the 43rd Annual Scientific Meeting, The committee on Problems of Drug Dependence, Inc.*, Harris, L. S. Eds.; Committee on Problems of Drug Dependence, Inc.: 1982; Vol. NIDA Research Monograph 41, pp. 112-118.

(31) Zimmerman, D. M.; Cantrell, B. E.; Swartzendruber, J. K.; Jones, N. D.; Mendelsohn, L. G.; Leander, J. D.; Nickander, R. C. Synthesis and analgesic properties of N-substituted trans-4a-aryldecahydroisoquinolines. *J. Med. Chem.* 1988, 31, 555-560.

(32) Zimmerman, D. M.; Leander, J. D.; Cantrell, B. E.; Reel, J. K.; Snoddy, J.; Mendelsohn, L. G.; Johnson, B. G.; Mitch, C. H. Structure-activity relationships of the trans-3,4-dimethyl-4-(3-hydroxyphenyl)piperidine antagonists for µ and κ opioid receptors. *J. Med. Chem.* 1993, 36(20), 2833-2841.

(33) Zimmerman, D. M.; Hermann, R. B.; Mitch, C. H.; Shaw, W. N.; Mendelsohn, L. G.; Leander, J. D. Opioid receptor antagonists: Comparison of trans-3,4-dimethyl-4-phenylpiperidines and their use in the development of a model of opioid receptors. *Pharmacol. Rev.* in press.

(34) Thomas, J. B.; Zheng, X.; MascareHa, S. W.; Rothman, R. B.; Dersch, C. M.; Partilla, J. S.; Flippen-Anderson, J. L.; George, C. F.; Cantrell, B. E.; Zimmerman, D. M.; Carroll, F. I. N-Substituted 9β-methyl-5-(3-hydroxyphenyl)morphans are opioid receptor pure antagonists. *J. Med. Chem.* 1998, 41(21), 4143-4149.

(35) Werner, J. A.; Cerbone, L. R.; Frank, S. A.; Ward, J. A.; Labib, P.; Tharp-Taylor, R. W.; Ryan, C. W. Synthesis of trans-3,4-dimethyl-4-(3-hydroxyphenyl)piperidine opioid antagonists: Application of the cis-thermal elimination of carbonates to alkaloid synthesis. *J. Org. Chem.* 1996, 61, 587-597.

(36) Gu, X.-P.; Ikeda, I.; Komada, S.; Masuyama, A.; Okahara, M. *J. Org. Chem.* 1986, 51, 5425.

(37) Gu, X.-P.; Nishida, N.; Ikeda, I.; Okahara, M. 2-(Chloromethyl)-3,5-dioxahex-1-ene. An effective acetonylating reagent. *J. Org. Chem.* 1987, 52, 3192-3196.

(38) Gu, X.-P.; Okuhara, T.; Ikeda, I.; Okahara, M. Catalytic acetonylation of cyclic 1,3-dicarbonyl-systems by 2-(chloromethyl)-3,5-dioxa-1-hexene. *Synthesis* 1988, 535-537.

(39) Thomas, J. B.; Gigstad, K. M.; Fix, S. E.; Burgess, J. P.; Cooper, J. B.; Mascarella, S. W.; Cantrell, B. E.; Zimmerman, D. M.; Carroll, F. I. A stereoselective synthetic approach to N-alkyl-4β-methyl-5-phenylmorphans. *Tetrahedron Lett.* 1999, 40(3), 403-406.

(40) Abdel-Magid, A. F.; Carson, K., G.; Harris, B. D.; Maryanoff, C. A.; Shah, R. D. Reductive animation of aldehydes and ketones with sodium triacetoxyborohydride. Studies on direct and indirect reductive animation procedures. *J. Org. Chem.* 1996, 61, 3849-3862.

(41) Bertha, C. M.; Ellis, M.; Flippen-Anderson, J. L.; Porreca, F.; Rothman, R. B.; Davis, P.; Xu, H.; Becketts, K.; Rice, K. C. Probes for narcotic receptor-mediated phenomena. 21. Novel derivatives of 3-(1,2,3,4,5,11-hexahydro-3-methyl-2,6-methano-6H-azocino[4,5-b]indol-6-yl)phenols with improved δ opioid receptor selectivity. *J. Med. Chem.* 1996, 39, 2081-2086.

(42) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and µ receptor subtype-selectivity in (+)-(3R,4R)-dimethyl-4-(3-hydroxyphenyl)piperidine opioid antagonists. *J. Med. Chem.* 1998, 41(11), 1980-1990.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of treating pain in a subject in need thereof, comprising:
   administering to said subject a composition comprising an opioid receptor agonist and a physiologically acceptable carrier, wherein the opioid receptor agonist is a compound of formula (I):

wherein $R_1$ is $C_{1-8}$ alkyl, $C_{3-8}$ alkenyl, $C_{3-8}$ alkynyl, $C_{1-8}$ alkylaryl or one of the following groups:

or —$(CH_2)_n$(Het), wherein (Het) is a member selected from

R is hydrogen, $C_{1-8}$ alkyl, $C_{3-8}$ alkenyl, $C_{3-8}$ alkynyl, $C_{1-8}$ alkylaryl, —$CO_2R_8$;
$R_2$ is H, halogen, $C_{1-4}$ alkyl, CN or $OCH_3$;
Y is OH, $OR_9$, $C_{1-8}$ alkyl, F, Cl, Br, $CF_3$ or CN;
W is a member selected from the group consisting of: H, OH, —$CO_2R_8$; amino, —$NR_3SO_2R_7$, —$NR_3CO_2R_7$, —$CONH_2$; and —NHCHO
n is 1, 2, 3 or 4;

$R_3$ is hydrogen, $C_{1-8}$ alkyl, $C_{3-8}$ alkenyl, $C_{3-8}$ alkynyl, $C_{1-8}$ alkylaryl, —CH$_2$Y or —CO$_2$R;

$R_4$ is hydrogen, $C_{1-8}$ alkyl, $C_{3-8}$ alkenyl, $C_{3-8}$ alkynyl, or $C_{1-8}$ alkylaryl;

$R_5$ and $R_6$ are each, independently, hydrogen, $C_{1-8}$ alkyl, $C_{3-8}$ alkenyl, $C_{3-8}$ alkynyl, or $C_{1-8}$ alkylaryl;

$R_7$ and $R_8$ are each independently, $C_{1-8}$ alkyl, $C_{3-8}$ alkenyl, $C_{3-8}$ alkynyl, or $C_{1-8}$ alkylaryl.

2. The method of claim 1, wherein said opioid receptor agonist is a compound of formula I:

wherein Y, W, n, $R_2$ and $R_8$ are as noted above;

$R_1$ is $C_{2-8}$ alkyl, $C_{3-8}$ alkenyl, or a group of the following formulae:

$R_3$ is hydrogen, or $C_{1-8}$ alkyl;

$R_4$ is hydrogen, or $C_{1-8}$ alkyl;

$R_5$ and $R_6$ are each independently, hydrogen, $C_{1-8}$ alkyl, or $C_{1-8}$ alkylaryl; and $R_7$ is $C_{1-8}$ alkyl, or $C_{1-8}$ alkylaryl.

3. The method of claim 1, wherein said opioid receptor agonist is a compound of formula I:

wherein Y, n, $R_2$ and $R_8$ are the same as noted above;

$R_1$ is $C_{2-8}$ alkyl, $C_{3-8}$ alkenyl, or a group selected from the following formulae:

W is OH or CO$_2$R$_8$;

$R_3$ is hydrogen, or $C_{1-4}$ alkyl;

$R_4$ is hydrogen or $C_{1-4}$ alkyl;

$R_5$ and $R_6$ are each independently, hydrogen, or $C_{1-4}$ alkyl; and $R_7$ is $C_{1-4}$ alkyl.

4. The method of claim 1, wherein said opioid receptor agonist is a compound of formula I:

wherein Y, n, $R_2$, and $R_9$ are as noted above;

$R_1$ is $C_{2-8}$ alkyl, $C_{3-8}$ alkenyl, $C_{1-4}$ alkylaryl or a member selected from the following formulae:

W is OH or CO$_2$R$_8$;

$R_3$ is hydrogen, or methyl;

$R_4$ is hydrogen or methyl;

$R_5$ and $R_6$ are each independently, hydrogen, or $C_{1-4}$ alkyl; and $R_7$ is $C_{1-4}$ alkyl.

5. The method of claim 1, wherein said opioid receptor agonist is a compound of formula 23:

6. An opioid receptor agonist compound represented by the formula (I):

wherein $R_1$ is $C_{1-8}$ alkyl, $C_{3-8}$ alkenyl, $C_{3-8}$ alkynyl, $C_{1-8}$ alkylaryl or one of the following groups:

-continued $$\overset{O}{\underset{}{C}}-\overset{R_7}{\underset{R_8}{C}}$$

or —$(CH_2)_n$(Het), wherein (Het) is a member selected from

[furan] and [thiophene];

R is hydrogen, $C_{1-8}$ alkyl, $C_{3-8}$ alkenyl, $C_{3-8}$ alkynyl, $C_{1-8}$ alkylaryl, —$CO_2R_8$;

$R_2$ is H, halogen, $C_{1-4}$ alkyl, CN or $OCH_3$;

Y is OH, $OR_9$, $C_{1-8}$ alkyl, F, Cl, Br, $CF_3$ or CN;

W is a member selected from the group consisting of: H, OH, —$CO_2R_8$; amino, —$NR_3SO_2R_7$, —$NR_3CO_2R_7$, —$CONH_2$; and —NHCHO n is 1, 2, 3 or 4;

$R_3$ is hydrogen, $C_{1-8}$ alkyl, $C_{3-8}$ alkenyl, $C_{3-8}$ alkynyl, $C_{1-8}$ alkylaryl, —$CH_2Y$ or —$CO_2R$;

$R_4$ is hydrogen, $C_{1-8}$ alkyl, $C_{3-8}$ alkenyl, $C_{3-8}$ alkynyl, or $C_{1-8}$ alkylaryl;

$R_5$ and $R_6$ are each, independently, hydrogen, $C_{1-8}$ alkyl, $C_{3-8}$ alkenyl, $C_{3-8}$ alkynyl, or $C_{1-8}$ alkylaryl, with the proviso that $R_5$ and $R_6$ cannot both be hydrogen;

$R_7$ and $R_8$ are each independently, $C_{1-8}$ alkyl, $C_{3-8}$ alkenyl, $C_{3-8}$ alkynyl, or $C_{1-8}$ alkylaryl.

7. The opioid receptor agonist of claim 6, wherein said opioid receptor agonist is a compound of formula I:

wherein Y, W, n, $R_2$ and $R_8$ are as noted above;

$R_1$ is $C_{2-8}$ alkyl, $C_{3-8}$ alkenyl, or a group of the following formulae:

—$(CH_2)_n$—[phenyl]—Y

—$(CH_2)_n$—C(O)—[phenyl]—Y

—$(CH_2)_n$—O—[phenyl]—Y $R_3$ is hydrogen, or $C_{1-8}$ alkyl;

$R_4$ is hydrogen, or $C_{1-8}$ alkyl;

$R_5$ and $R_6$ are each independently, hydrogen, $C_{1-8}$ alkyl, or $C_{1-8}$ alkylaryl, with the proviso that $R_5$ and $R_6$ cannot both be hydrogen; and $R_7$ is $C_{1-8}$ alkyl, or $C_{1-8}$ alkylaryl.

8. The opioid receptor agonist of claim 6, wherein said opioid receptor agonist is a compound of formula I:

wherein Y, n, $R_2$ and $R_8$ are the same as noted above;

$R_1$ is $C_{2-8}$ alkyl, $C_{3-8}$ alkenyl, or a group selected from the following formulae:

—$(CH_2)_n$—[phenyl]—Y

—$(CH_2)_n$—C(O)—[phenyl]—Y

—$(CH_2)_n$—O—[phenyl]—Y

W is OH or $CO_2R_8$;

$R_3$ is hydrogen, or $C_{1-4}$ alkyl;

$R_4$ is hydrogen or $C_{1-4}$ alkyl;

$R_5$ and $R_6$ are each independently, hydrogen, or $C_{1-4}$ alkyl, with the proviso that $R_5$ and $R_6$ cannot both be hydrogen; and $R_7$ is $C_{1-4}$ alkyl.

9. The opioid receptor agonist of claim 6, wherein said opioid receptor agonist is a compound of formula I:

wherein Y, n, $R_2$, and $R_9$ are as noted above;

$R_1$ is $C_{2-8}$ alkyl, $C_{3-8}$ alkenyl, $C_{1-4}$ alkylaryl or a member selected from the following formulae:

—$(CH_2)_n$—[phenyl]—Y

—$(CH_2)_n$—C(O)—[phenyl]—Y

—$(CH_2)_n$—O—[phenyl]—Y

W is OH or $CO_2R_8$;

$R_3$ is hydrogen, or methyl;

$R_4$ is hydrogen or methyl;

$R_5$ and $R_6$ are each independently, hydrogen, or $C_{1-4}$ alkyl, with the proviso that $R_5$ and $R_6$ cannot both be hydrogen; and $R_7$ is $C_{1-4}$ alkyl.

10. A pharmaceutical composition comprising:

an effective amount of an opioid receptor agonist and a physiologically acceptable carrier, wherein the opioid receptor agonist is a compound of formula (I):

(I)

[structure of formula I with substituents W, $R_2$, $R_3$, $R_4$, $R_5$, $R_6$, $R_1$]

wherein $R_1$ is $C_{1-8}$ alkyl, $C_{3-8}$ alkenyl, $C_{3-8}$ alkynyl, $C_{1-8}$ alkylaryl or one of the following groups:

or —(CH$_2$)$_n$(Het), wherein (Het) is a member selected from

R is hydrogen, C$_{1-8}$ alkyl, C$_{3-8}$ alkenyl, C$_{3-8}$ alkynyl, C$_{1-8}$ alkylaryl, —CO$_2$R$_8$;
R$_2$ is H, halogen, C$_{1-4}$ alkyl, CN or OCH$_3$;
Y is OH, OR$_9$, C$_{1-8}$ alkyl, F, Cl, Br, CF$_3$ or CN;
W is a member selected from the group consisting of: H, OH, —CO$_2$R$_8$; amino, —NR$_3$SO$_2$R$_7$, —NR$_3$CO$_2$R$_7$, —CONH$_2$; and —NHCHO
n is 1, 2, 3 or 4;
R$_3$ is hydrogen, C$_{1-8}$ alkyl, C$_{3-8}$ alkenyl, C$_{3-8}$ alkynyl, C$_{1-8}$ alkylaryl, —CH$_2$Y or —CO$_2$R;
R$_4$ is hydrogen, C$_{1-8}$ alkyl, C$_{3-8}$ alkenyl, C$_{3-8}$ alkynyl, or C$_{1-8}$ alkylaryl;
R$_5$ and R$_6$ are each, independently, hydrogen, C$_{1-8}$ alkyl, C$_{3-8}$ alkenyl, C$_{3-8}$ alkynyl, or C$_{1-8}$ alkylaryl;
R$_7$ and R$_8$ are each independently, C$_{1-8}$ alkyl, C$_{3-8}$ alkenyl, C$_{3-8}$ alkynyl, or C$_{1-8}$ alkylaryl.

11. The pharmaceutical composition of claim 10, wherein said opioid receptor agonist is a compound of formula I:
wherein Y, W, n, R$_2$ and R$_8$ are as noted above;
R$_1$ is C$_{2-8}$ alkyl, C$_{3-8}$ alkenyl, or a group of the following formulae:

R$_3$ is hydrogen, or C$_{1-8}$ alkyl;
R$_4$ is hydrogen, or C$_{1-8}$ alkyl;
R$_5$ and R$_6$ are each independently, hydrogen, C$_{1-8}$ alkyl, or C$_{1-8}$ alkylaryl; and
R$_7$ is C$_{1-8}$ alkyl, or C$_{1-8}$ alkylaryl.

12. The pharmaceutical composition of claim 10, wherein said opioid receptor agonist is a compound of formula I:
wherein Y, n, R$_2$ and R$_8$ are the same as noted above;
R$_1$ is C$_{2-8}$ alkyl, C$_{3-8}$ alkenyl, or a group selected from the following formulae:

W is OH or CO$_2$R$_8$;
R$_3$ is hydrogen, or C$_{1-4}$ alkyl;
R$_4$ is hydrogen or C$_{1-4}$ alkyl;
R$_5$ and R$_6$ are each independently, hydrogen, or C$_{1-4}$ alkyl; and
R$_7$ is C$_{1-4}$ alkyl.

13. The pharmaceutical composition of claim 10, wherein said opioid receptor agonist is a compound of formula I:
wherein Y, n, R$_2$, and R$_9$ are as noted above;
R$_1$ is C$_{2-8}$ alkyl, C$_{3-8}$ alkenyl, C$_{1-4}$ alkylaryl or a member selected from the following formulae:

W is OH or CO$_2$R$_8$;
R$_3$ is hydrogen, or methyl;
R$_4$ is hydrogen or methyl;
R$_5$ and R$_6$ are each independently, hydrogen, or C$_{1-4}$ alkyl; and
R$_7$ is C$_{1-4}$ alkyl.

14. The pharmaceutical composition of claim 10, wherein said opioid receptor agonist is a compound of formula 23:

(23)

15. The pharmaceutical composition of claim 10, wherein said composition is an injectable composition.

16. The pharmaceutical composition of claim 10, wherein said composition is an orally administrable composition.

17. The pharmaceutical composition of claim 16, wherein said orally administrable composition is in a form selected from the group consisting of tablets, capsules, troches, powders, solutions, dispersions, emulsions and suspensions.

18. The pharmaceutical composition of claim 10, wherein $R_5$ and $R_6$ cannot both be hydrogen.

* * * * *

UNITED STATES PATENT AND TRADEMARK OFFICE
CERTIFICATE OF CORRECTION

PATENT NO.       : 7,399,762 B2
APPLICATION NO.  : 11/113158
DATED            : July 15, 2008
INVENTOR(S)      : Frank I Carroll et al.

It is certified that error appears in the above-identified patent and that said Letters Patent is hereby corrected as shown below:

Column 10, line 38, "5-(3-Isopropoxyphenyl)-2,4-dimethyl    -2-aza-bicyclo"
    should read -- 5-(3-Isopropoxyphenyl)-2,4-dimethyl-2-aza-bicyclo --;
      line 49, "dried dried ($Na_2SO_4$),"
  should read -- dried ($Na_2SO_4$), --.

Column 11, line 28, "This product was used with out"
  should read -- This product was used without --.

Column 12, line 8, "filtered, and concentrated in vacuu."
  should read -- filtered, and concentrated *in vacuu.* --.

Signed and Sealed this

Thirtieth Day of December, 2008

JON W. DUDAS
*Director of the United States Patent and Trademark Office*